United States Patent
Yahiaoui et al.

(10) Patent No.: US 6,613,703 B1
(45) Date of Patent: Sep. 2, 2003

(54) THERMOPLASTIC NONWOVEN WEB CHEMICALLY REACTED WITH A CYCLODEXTRIN COMPOUND

(75) Inventors: Ali Yahiaoui, Roswell, GA (US); Tami Lynette O'Connell, Roswell, GA (US); David Lewis Myers, Cumming, GA (US); Charles Edward Bolian, II, Buford, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/559,568

(22) Filed: Apr. 27, 2000

(51) Int. Cl.[7] .............................. B32B 27/04; B32B 9/04; B32B 5/02; B32B 23/02; B32B 3/26; B32B 5/14; D21H 13/00

(52) U.S. Cl. ........................ 442/76; 442/118; 442/153; 442/154; 442/155; 442/165; 428/305.5; 428/308.8; 428/311.51

(58) Field of Search ............................. 442/62, 65, 76, 442/85, 86, 93, 96, 118, 121, 123, 124, 125, 131, 152, 153, 154, 155, 164, 165, 166, 173, 174; 428/305.5, 308.8, 311.51

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,426,004 A | 2/1969 | Wagner | 260/80.3 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,615,865 A | 10/1971 | Wetherell | 136/146 |
| 3,692,618 A | 9/1972 | Dorschner et al. | 161/72 |
| 3,765,948 A | 10/1973 | Johnson et al. | 136/146 |

(List continued on next page.)

FOREIGN PATENT DOCUMENTS

| | | | |
|---|---|---|---|
| EP | 0 710 994 A2 | 5/1996 | H01M/2/16 |
| EP | 703 308 B1 | 6/1999 | D04H/13/00 |
| JP | 62265302 A | 11/1987 | C08F/2/50 |
| JP | 3221501 A | 9/1991 | C08B/37/16 |
| JP | 10259202 A | 9/1998 | C08B/37/16 |
| WO | 93/01622 | 1/1993 | H01M/2/16 |
| WO | 96/00260 | 1/1996 | C08L/101/00 |
| WO | 09662 | 3/1998 | A61L/15/20 |
| WO | 10134 | 3/1998 | D06M/15/03 |
| WO | 04831 | 2/1999 | A61L/15/48 |
| WO | 05357 | 2/1999 | D06M/15/03 |

OTHER PUBLICATIONS

DeLucia et al., Non–woven materials with time release additives US 2001/0031938 A1 Publication date Oct. 18, 2001 Filing Date: Dec. 4, 2000 Related US data: Non–provisional of provisional application filed on Dec. 23, 1999.*

Manson, John A. and Sperling, Leslie H.: *Polymer Blends and Composites*, Plenum Press, New York, ISBN 0–306–30831–2, pp. 273–277 (1976).

Shuichi Matsumura, et al., *Surface Activities, Biodegradability and Antimicrobial Poperties of n–Alkyl Glucosides, Mannosides and Galactosides*, JAOCS, vol. 67, No. 12, pp. 996–1001 (Dec. 1990).

*Primary Examiner*—Terrel Morris
*Assistant Examiner*—Lynda Salvatore
(74) *Attorney, Agent, or Firm*—Pauley Peterson Kinne & Erickson

(57) ABSTRACT

A cyclodextrin-modified thermoplastic porous layer material is prepared by coating the surface of a fibrous nonwoven web, open-celled foam, porous film or the like with a chemical composition including a cyclodextrin compound, and then irradiating the coated fabric to induce a chemical reaction between the cyclodextrin compound and the underlying layer material. The resulting cyclodextrin-modified layer material has durable hydrophilic properties useful in topsheets for absorbent articles, and entrapment capabilities useful in water filters, blood filters, controlled delivery articles and protective garments.

34 Claims, 1 Drawing Sheet

U.S. PATENT DOCUMENTS

| | | | |
|---|---|---|---|
| 3,802,817 A | 4/1974 | Matsuki et al. | 425/66 |
| 3,849,241 A | 11/1974 | Butin et al. | 161/169 |
| 4,000,967 A | 1/1977 | Johnson et al. | 8/115.5 |
| 4,110,143 A | 8/1978 | Cogliano et al. | 156/167 |
| 4,218,280 A | 8/1980 | Philipp et al. | 156/272 |
| 4,234,623 A | 11/1980 | Moshtev et al. | 427/54.1 |
| 4,273,786 A | 6/1981 | Kraskin | 424/319 |
| 4,273,840 A | 6/1981 | Machi et al. | 429/144 |
| 4,287,276 A | 9/1981 | Lundquist, Jr. et al. | 429/206 |
| 4,298,666 A | 11/1981 | Taskier | 429/206 |
| 4,320,040 A | 3/1982 | Fujita et al. | 524/459 |
| 4,340,563 A | 7/1982 | Appel et al. | 264/518 |
| 4,438,185 A | 3/1984 | Taskier | 429/250 |
| 4,731,304 A | 3/1988 | Lundquist et al. | 429/62 |
| 4,775,582 A | 10/1988 | Abba et al. | 428/288 |
| 4,797,190 A | 1/1989 | Peck | 204/296 |
| 4,975,217 A | 12/1990 | Brown-Skrobot et al. | 252/107 |
| 5,001,176 A | 3/1991 | Nakazima | 524/48 |
| 5,049,275 A | 9/1991 | Gillberg-LaForce et al. | 210/500.27 |
| 5,108,820 A | 4/1992 | Kaneko et al. | 428/198 |
| 5,108,827 A | 4/1992 | Gessner | 428/219 |
| 5,126,219 A | 6/1992 | Howard et al. | 429/252 |
| 5,202,183 A | 4/1993 | Hosako et al. | 428/364 |
| 5,204,197 A | 4/1993 | Takai et al. | 429/249 |
| 5,206,325 A | 4/1993 | Hata et al. | 527/305 |
| 5,230,949 A | 7/1993 | Howard et al. | 428/224 |
| 5,271,883 A | 12/1993 | Timmons et al. | 264/6 |
| 5,276,088 A | 1/1994 | Yoshinaga | 525/54.3 |
| 5,290,645 A | 3/1994 | Tanaka et al. | 429/144 |
| 5,336,552 A | 8/1994 | Strack et al. | 428/224 |
| 5,336,573 A | 8/1994 | Zuckerbrod et al. | 429/252 |
| 5,354,617 A | 10/1994 | Ikkanzaka et al. | 428/397 |
| 5,357,012 A | 10/1994 | Nussstein et al. | 526/238.2 |
| 5,362,582 A | 11/1994 | Chang et al. | 429/249 |
| 5,382,400 A | 1/1995 | Pike et al. | 264/168 |
| 5,464,687 A | 11/1995 | Sheth | 428/286 |
| 5,487,944 A | 1/1996 | Ikkanzaka et al. | 428/374 |
| 5,492,947 A | 2/1996 | Wood et al. | 524/48 |
| 5,589,302 A | 12/1996 | Degen et al. | 429/250 |
| 5,603,974 A | 2/1997 | Wood et al. | 426/415 |
| 5,608,015 A | 3/1997 | Yoshinaga | 526/75 |
| 5,612,389 A | 3/1997 | Chabrecek et al. | 522/35 |
| 5,612,391 A | 3/1997 | Chabrecek et al. | 523/106 |
| 5,633,368 A * | 5/1997 | Hirsenkorn | 536/103 |
| 5,654,422 A | 8/1997 | Hirsenkorn | 536/103 |
| 5,656,361 A | 8/1997 | Vogt et al. | 428/198 |
| 5,688,855 A * | 11/1997 | Stoy et al. | 524/505 |
| 5,709,951 A | 1/1998 | Sato et al. | 428/430 |
| 5,770,549 A | 6/1998 | Gross | 510/238 |
| 5,789,461 A | 8/1998 | Nicolson et al. | 523/106 |
| 5,849,411 A | 12/1998 | Nohr et al. | 428/378 |
| 5,849,811 A | 12/1998 | Nicolson et al. | 523/106 |
| 5,856,416 A | 1/1999 | Bachmann et al. | 526/238.23 |
| 5,882,565 A | 3/1999 | Wood et al. | 264/209.5 |
| 5,888,524 A | 3/1999 | Cole | 424/402 |
| 5,889,073 A | 3/1999 | Zhang et al. | 522/3 |
| 5,897,960 A | 4/1999 | Oba et al. | 428/532 |
| 5,902,799 A | 5/1999 | Herrmann et al. | 514/58 |
| 5,932,495 A | 8/1999 | Boney et al. | 442/121 |
| 5,939,466 A | 8/1999 | Bachmann et al. | 523/106 |
| 5,951,534 A | 9/1999 | Cummings et al. | 604/359 |
| 5,965,631 A | 10/1999 | Nicolson et al. | 523/106 |
| 5,968,404 A | 10/1999 | Trinh et al. | 252/8.91 |
| 5,985,772 A * | 11/1999 | Wood et al. | 442/70 |
| 6,433,243 B1 * | 8/2002 | Woltman et al. | 604/359 |

* cited by examiner

THERMOPLASTIC NONWOVEN WEB CHEMICALLY REACTED WITH A CYCLODEXTRIN COMPOUND

FIELD OF THE INVENTION

This invention is directed to a thermoplastic nonwoven web of fibers having a cyclodextrin compound chemically reacted with the thermoplastic polymer. The chemical reaction imparts durable hydrophilic properties to the fiber surfaces.

BACKGROUND OF THE INVENTION

Water-permeable nonwoven fabrics, porous films, open-celled foams, and other layer materials and their manufacture have been the subject of extensive development resulting in a wide variety of materials for numerous applications. For example, nonwovens of light basis weight and open structure are used in personal care items such as disposable diapers as liner fabrics that provide dry skin contact but readily transmit fluids to more absorbent materials which may also be nonwovens of a different composition and/or structure. Nonwovens of heavier weights may be designed with pore structures making them suitable for filtration, absorbent and barrier applications such as wrappers for items to be sterilized, wipers or protective garments for medical, veterinary or industrial uses. Even heavier weight nonwovens have been developed for recreational, agricultural and construction uses. Water-permeable porous thermoplastic films are also employed in some of these applications, and may be combined with nonwoven webs. Open-celled foams are also useful in some applications.

It is not always possible to efficiently produce a porous, water-permeable layer material having all the desired properties as formed, and it is frequently necessary to treat the material with a surfactant to improve or alter surface properties such as wettability by one or more fluids, repellency to one or more fluids, electrostatic characteristics, conductivity, and softness, to name just a few examples. Conventional surfactant treatments involve steps such as dipping the substrate in a treatment bath, coating or spraying the substrate with the treatment composition, and printing the substrate with the treatment composition. For cost and other reasons it is usually desired to use the minimum amount of treatment composition that will produce the desired effect with an acceptable degree of uniformity.

For many thermoplastic layer material end use applications, it is desirable to reduce, prevent, or eliminate odors. For diapers and other incontinence products, it is desirable to reduce or eliminate the odor of ammonia which is present in urine. For feminine hygiene products, it is desirable to reduce or eliminate the odor of triethylamine. Other common odor-producing substances include isovaleric acid, dimethyl disulfide, and dimethyl trisulfide.

Odor control agents include odor inhibitors, odor absorbers, and other compounds which reduce, prevent, or eliminate odors. Odor inhibitors prevent the odor from forming. For example, U.S. Pat. No. 4,273,786 to Kraskin teaches the use of an aminopolycarboxylic acid compound for inhibiting the formation of ammonia from urea in urine. Odor absorbers and adsorbers remove odor after it is formed. Examples of odor control agents that remove odor by absorption or adsorption include activated carbon, silica, and cyclodextrins.

Typical odor control agents based on cyclodextrins cannot easily be applied from aqueous solutions to water-permeable thermoplastic substrates such as polyolefin nonwoven fabrics, porous films, and open-celled foams because the surface tension of these solutions is too high to wet out the hydrophobic substrate. Personal care products such as diapers and feminine care pads typically contain polyolefin nonwoven fabrics and/or other porous thermoplastic cover layers. Therefore, typical odor control agents cannot usually be applied to the porous thermoplastic components of personal care products. Instead, these odor control agents are usually introduced as powders to the product, which has several drawbacks. For example, placement and containment of the powder in the product can be troublesome. More importantly, powders do not present optimum surface area for odor absorption due to a rather low surface to volume ratio. Therefore, more odor control agent will be needed if in powder form. Furthermore, odor control and hydrophilic modifiers applied in powder form, or as surface treatments, are often not desirable and can be washed away.

There is a need or desire for odor absorbing compounds, hydrophilic modifiers, antistatic agents, and the like which can be applied to a water-permeable hydrophobic (e.g., thermoplastic) substrate in a manner which optimizes the coating over the target surface area, and which prevents easy washing/removal of the compounds.

Nonwoven polymer-based battery separators are also known in the art. U.S. Pat. No. 5,589,302, issued to Degen et al., discloses a battery separator including a nonwoven web of fibers having a mean diameter of about 15 microns or less, and a graft polymerized monomer on the surface of the nonwoven web which renders the web spontaneously wettable by an alkaline electrolyte. The nonwoven web includes a mixture of two polymers having different melting points. The monomers suitable for grafting include vinyl sulfonic acid, vinyl phosphonic acid, and acrylic and methacrylic acid and hydroxyl functional derivatives thereof. The grafting is effected by irradiating the nonwoven web in the absence of oxygen, before or during exposing the web to a solution of the monomer. The use of E-beam radiation is disclosed.

One disadvantage of the above battery separators is that some of the residual monomer and ungrafted oligomers may leach out during prolonged exposure to the battery electrolyte. This leaching contaminates the electrolyte, and is detrimental to the performance of the battery cell. The leaching is largely attributable to: a) incomplete chemical reactions, b) competing homopolymerization reactions, and c) residual catalysts. There is a need or desire for a polymeric nonwoven web-based battery separator which has a greater affinity for the monomer, and which contains less unreacted monomer. There is also a need or desire for a process of making a battery separator, which facilitates a more complete reaction between the wettable monomer and/or polymer and the polyolefin fibers.

SUMMARY OF THE INVENTION

The present invention is a thermoplastic water-permeable layer material, such as nonwoven fibrous web, in which the thermoplastic polymer has been chemically reacted (e.g., grafted) with a cyclodextrin compound. Suitable cyclodextrin compounds include methacryloyl-R-cyclodextrins, where R is an alkyl group having 2 to 20 carbon atoms; acryloyl-R-cyclodextrins, where R is an alkyl group having 1 to 20 carbon atoms; alkenyl succinylated cyclodextrins, where the alkenyl group has 2 to 20 carbon atoms; and the like. The cyclodextrin compounds can have a degree of substitution ranging from 0.1 to 7. The compounds can be based on any known cyclodextrin having 6 to 12 glucose units arranged in a ring, including without limitation an alpha-cyclodextrin (having 6 glucose units), a beta-cyclodextrin (having 7 glucose units), a gamma-cyclodextrin (having 8 glucose units), or a combination including one or more of the foregoing.

The cyclodextrin-modified nonwoven web has durable hydrophilic properties and odor control which are useful in personal care absorbent articles and protective garments. The cyclodextrin-modified nonwoven web can also be used for a battery separator, for selective filtration of organic molecules, and as a delivery system for drugs, fragrances, bioactive agents, catalysts, dyes, brighteners, and other compounds. When used as a battery separator, the grafted substrate remains hydrophilic and functional in a highly oxidizing medium, for instance, a 40% potassium hydroxide aqueous solution. When used as a filter or delivery system, small molecules can be temporarily hindered or trapped inside the cyclodextrin cavities, each of which is formed by a ring of glucose units. Because of the chemical reaction, the improved properties of the nonwoven web are durable, and the cyclodextrin compound cannot be easily washed away or otherwise removed.

With the foregoing in mind, it is a feature and advantage of the invention to provide a cyclodextrin-modified thermoplastic water-permeable layer material, such as a fibrous nonwoven web, in which a cyclodextrin compound is chemically reacted with the thermoplastic polymer.

It is also a feature and advantage of the invention to provide a method of making the cyclodextrin-modified water-permeable layer material.

DEFINITIONS

Figure 1:
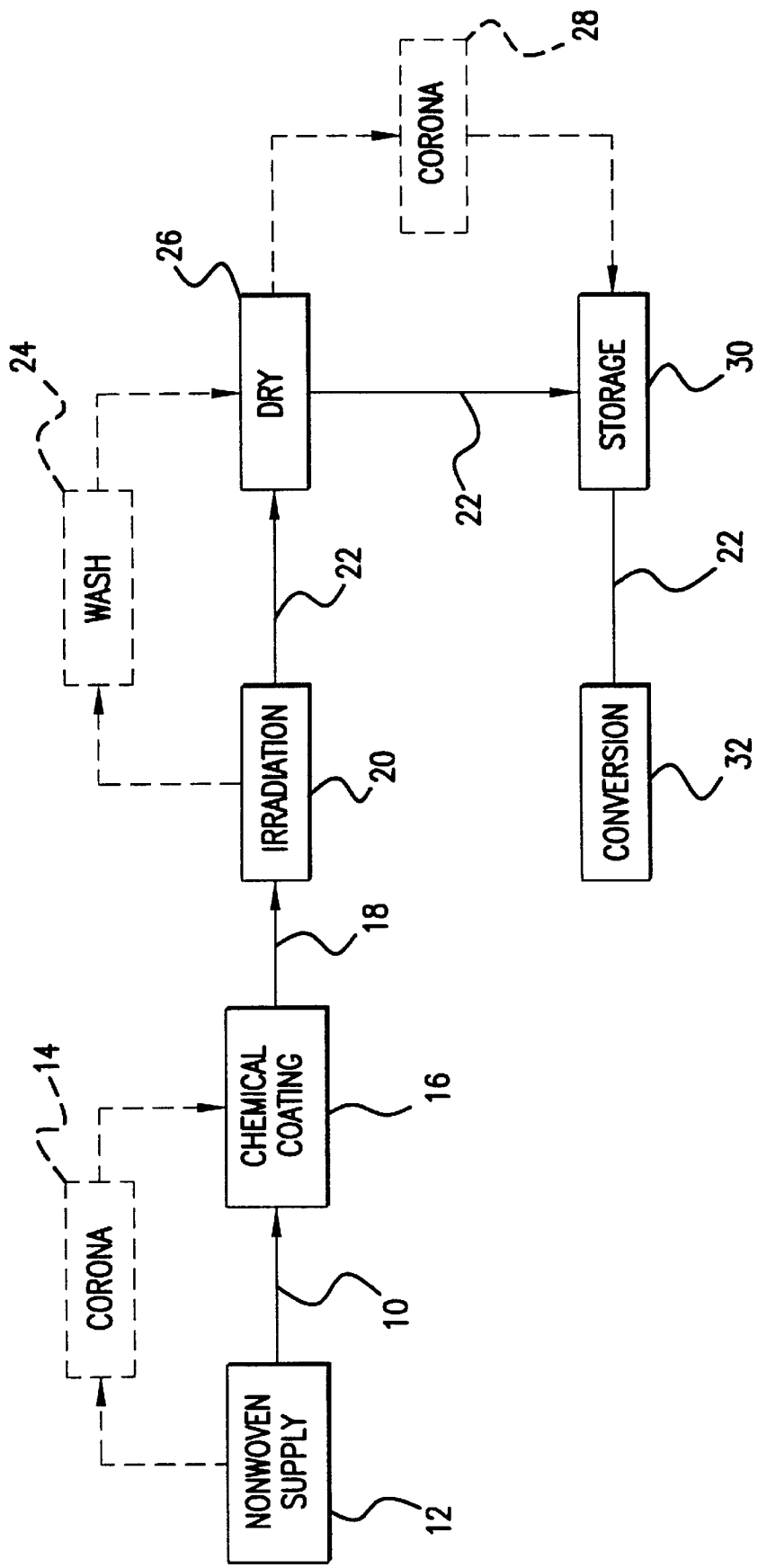
FIG. 1 schematically illustrates a process for preparing a cyclodextrin-modified water-permeable porous layer material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, microfibers may have an average diameter of from about 1 micron to about 30 microns. Another frequently used expression of fiber diameter is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "coform" material refers to a product containing about 10–90% by weight of thermoplastic meltblown fibers and about 10–90% by weight of staple-length pulp fibers dispersed within the meltblown fiber matrix. More commonly, coform materials contain about 20–70% by weight thermoplastic meltblown fibers and about 30–80% by weight pulp fibers.

The term "film" refers to a thermoplastic film made using a film extrusion process, such as a cast film or blown film extrusion process.

The term "water-permeable porous film" includes films, such as thermoplastic polymer-containing films, which permit the flow of water through open or inter-connected pores. The term includes films rendered porous by puncturing or aperturing, and to films rendered porous by mixing polymer with filler, forming a film from the mixture, and stretching the film sufficiently to form liquid passages through the film.

The term "open-celled foam material" refers to a layer material made with the aid of a foaming process, in which the cells in the foam create open pores from one surface of the layer to the opposite surface. The term does not include foams which substantially block the flow of liquid water, such as closed-cell foam materials.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "water-permeable porous layer material" refers to a material present in one or more layers, such as a film, nonwoven fabric, or open-celled foam, which is porous, and which is water-permeable due to the flow of water and other aqueous liquids, through the pores. The pores in the film or foam, or spaces between fibers or filaments in a nonwoven web, are large enough and frequent enough to permit leakage and flow of liquid water through the material. The term does not include films and other materials which block the transfer of water, or which permit the transfer only by molecular diffusion.

The term "superabsorbent material" refers to a water-swellable, water-insoluble organic or inorganic material capable, under the most favorable conditions, of absorbing at least about 20 times its weight, preferably at least about 30 times its weight in an aqueous solution containing 0.9% by weight sodium chloride.

The term "ion exchange membrane" includes battery separators as well as membranes used in water treatment, which are receptive to highly alkaline electrolytes and are durable in highly alkaline environments.

The term "personal care absorbent article" includes without limitation diapers, training pants, swim wear, absorbent underpants, baby wipes, adult incontinence products, and feminine hygiene products.

The term "protective garment" includes without limitation medical garments, underpads, bandages, absorbent drapes, and medical wipes, as well as industrial work wear garments.

The term "hydrophilic" or "wettable" means that the polymeric material has an apparent surface free energy such that the polymeric material is wettable by an aqueous medium (i.e., a liquid medium of which water is a major component). That is, an aqueous medium wets the nonwoven fabric. "Apparent surface free energy" refers to the highest surface tension of an aqueous liquid which wets the polymeric material. For example, the apparent surface free energy of a polymeric material that is wetted by an aqueous liquid having a surface tension of 72 dynes/cm, is at least 72 dynes/cm and possibly higher. In the fabrics of the invention, a surface of the nonwoven fabric has been grafted with a polymerizable cyclodextrin complexing agent using radiation-induced grafting techniques as described below.

The term "cyclodextrin compound" includes any compound which includes the cyclodextrin ring structure, including derivatives of cyclodextrins that maintain the ring structure. The ring structure may be that of an alpha-cyclodextrin compound (6 glucose units), a beta-cyclodextrin compound (7 glucose units), a gamma cyclodextrin compound (8 glucose units), or a combination including compounds having one or more of these ring structures.

DETAILED DESCRIPTION OF THE PRESENTLY PREFERRED EMBODIMENTS

The invention is a thermoplastic water permeable porous layer material, in which at least some of the thermoplastic polymer has been chemically reacted with a cyclodextrin compound. The starting material for the invention is a water-permeable layer material. For instance, the starting material for the invention may be a porous thermoplastic layer or multilayer material capable of transmitting water (and other aqueous liquids) through the pores. Examples of suitable starting materials include thermoplastic fibrous nonwoven webs, open-celled foam layers, and thermoplastic polymer-containing films which are apertured or otherwise rendered porous, such as by stretching a film made from a mixture of a thermoplastic material and a particulate filler.

Suitable starting materials for the invention include nonwoven webs including a plurality of filaments made from one or more polymers. The nonwoven web may be a spunbond web, a meltblown web, a bonded carded web, or another type of nonwoven web, and may be present in a single layer or a multilayer composite including one or more nonwoven web layers and, in some instances, one or more film or foam layers. The web may include monocomponent or bicomponent filaments, or a combination including one or both filament types. The nonwoven web may have a variety of basis weights, preferably ranging from about 0.1–200 grams per square meter (gsm), suitably about 10–120 gsm, desirably about 40–80 gsm. One suitable nonwoven web is a polyolefin spunbond web. Another is a coform material, which includes a matrix of polyolefin meltblown fibers and a large percentage (often 30–80% by weight) of pulp fibers dispersed in the matrix of the meltblown fibers. Another suitable nonwoven web is an airlaid web of polyolefin fibers and pulp fibers.

A wide variety of hydrophobic thermoplastic polymers may be used to construct the starting porous layer material, including without limitation, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, hydrophobic polyurethanes, A-B block copolymers where A is formed of poly(vinyl arene) moieties such as polystyrene and B is an elastomeric midblock such as a conjugated diene or lower alkene, polyethers, polyether esters, polyisobutylene, poly-1-butene, copolymers of poly-1-butene including ethylene-1-butene copolymers, polybutadiene, isobutylene-isoprene copolymers, and combinations of any of the foregoing. Polyolefins are suitable. Polyethylene and polypropylene homopolymers and copolymers are particularly suitable.

The starting material is chemically reacted with a cyclodextrin compound. Suitable cyclodextrin compounds include compounds derived from cyclodextrins containing from six to twelve glucose units, including without limitation alpha-cyclodextrins (6 glucose units arranged in a ring), beta-cyclodextrins (7 glucose units arranged in a ring), and gamma-cyclodextrins (8 glucose units arranged in a ring). The coupling and configuration of the glucose units causes the cyclodextrins to have a conical molecular structure with a hollow interior lined by hydrogen atoms and glycosidic bridging oxygen atoms.

The cyclodextrin compound should be capable of reacting chemically with the hydrophobic thermoplastic polymer of the porous layer material, for instance, with the fibers of the hydrophobic thermoplastic nonwoven web. Suitable cyclodextrin compounds include methacryloyl-R-cyclodextrins, where R is an alkyl group having 2–20 carbon atoms, desirably 4 to 10 carbon atoms; acryloyl-R-cyclodextrins, where R is an alkyl group having 1 to 20 carbon atoms, desirably 4 to 10 carbon atoms; alkenyl succinylated cyclodextrins, where the alkenyl group has 2 to 20 carbon atoms, desirably 4 to 10 carbon atoms; and the like. The cyclodextrin compound may have a degree of substitution ranging from about 0.1 to about 7. Particularly suitable cyclodextrin compounds include methacryloyl-beta-cyclodextrins. One presently preferred cyclodextrin compound is 2-hydroxy-3-methylacryloyloxy-propyl-beta cyclodextrin (herein referred to as "HMPC").

The cyclodextrin compound may be chemically reacted with the hydrophobic thermoplastic polymer of the water-permeable porous layer material, using a variety of methods. In one suitable method, the hydrophobic water-permeable porous layer material is dipped into, and saturated with a chemical solution containing the cyclodextrin compound. The saturated layer material is then lightly pressed, for instance between two rubber nip rollers, to remove excess solution and ensure uniform surface coverage in the porous layer material. Then, the coated porous layer material is subjected to irradiation from an electron (E) beam source to induce the chemical reaction between the hydrophobic thermoplastic polymer and the cyclodextrin compound. E-beam radiation involves aiming electrons onto the surface of the coated layer material at high speeds, to generate free radicals which induce polymerization and the chemical reaction. Radiation levels of about 0.1–10 mrad may be employed. Suitably, the radiation level will be about 1–8 mrad, desirably about 2–5 mrad. Excessive radiation can cause excessive degradation of the cyclodextrin-modified porous layer material. Inadequate radiation results in incomplete surface grafting and too little crosslinking, making the effects less permanent.

E-beam radiation may be supplied using an ESI EB Curing System available from Energy Sciences, Inc. The amount of energy required to generate the radiation may vary with the line speed of the coated layer material. For instance, the line speed may range from about 20–2000 feet per minute. The energy may be varied by adjusting the accelerating voltage and/or current settings on the EB Curing System, or by allowing these parameters to self-adjust to provide the desired radiation levels for a given line speed. The accelerating voltage, for instance, may range from about 80–300 kV and is typically from about 80–250 kV. The current input may range from about 1–15 mA and is typically about 3–10 mA.

Gamma radiation may be employed as an alternative to E-beam radiation. Ultraviolet and/or X-ray radiation may also be employed. The use of radiation to facilitate the chemical reactions is preferred over chemical catalysts. Chemical catalysts may leave by-products which break down during subsequent use of the cyclodextrin-modified water-permeable layer material.

The chemical solution used to coat the nonwoven web is preferably an aqueous solution containing about 50–99% by weight water, preferably about 60–98% by weight water, most preferably about 70–97% by weight water. Other suitable solvents may also be employed. Hence, the composition contains about 1–50% by weight chemical solids, preferably about 2–40% by weight chemical solids, most preferably about 3–30% by weight chemical solids.

The chemical solution or mixture includes about 0.01–10% of the cyclodextrin compound, suitably about 0.05–5% by weight of the cyclodextrin compound, desirably about 0.1–1% of the cyclodextrin compound. These ranges are suitable for a chemical solution into which the nonwoven web is dipped and saturated, as described above, before being irradiated. Desirable ranges of composition may vary for different application techniques. On a dry basis, these percentages can be expressed as "parts by weight" of the dry chemical composition.

The chemical solution may also include other optional ingredients which add desirable properties to the nonwoven web, and which combine with the cyclodextrin compound to form a hydrogel layer having higher functionality. These other ingredients include polyacrylic acid, which augments the hydrophilic properties imparted to the web. The chemical solution may contain about 0–25% by weight polyacrylic acid, suitably about 0.5–15% by weight, desirably about 1–5% by weight. On a dry basis, these percentages can also be expressed as "parts by weight" of the dry chemical composition.

The chemical solution may also contain polyethylene glycol and/or polyvinyl alcohol which act as emulsifiers/surfactants to enhance the wettability of the nonwoven web and facilitate a more uniform coating, as well as enhancing crosslinking during subsequent irradiation. The chemical solution may contain about 0–10% by weight of the polyethylene glycol, suitably about 0.01–5% by weight, desirably about 0.1–1% by weight. The chemical solution may contain about 0–10% by weight of the polyvinyl alcohol, suitably about 0.01–5% by weight, desirably about 0.1–1% by weight. On a dry basis, these percentages can also be expressed as "parts by weight" of the dry chemical composition.

The chemical solution may also contain about 0.1–5% by weight hexanol, which acts as a wetting agent for the solution on the nonwoven web. Suitably, the chemical solution contains about 0.3–3% by weight hexanol, desirably about 0.5–1% by weight.

The chemical solution may also include about 0–10% by weight acrylic acid, suitably about 0.3–5% by weight, desirably about 0.5–3% by weight. During irradiation, the acrylic acid and polyacrylic acid both graft copolymerize onto the nonwoven web polymer. The polyacrylic acid crosslinks with itself and/or the polyvinyl alcohol. Again, these percentages may be expressed as parts by weight of a dry chemical composition.

The chemical solution preferably includes about 0.1–5.0% by weight hexanol, more preferably about 0.2–1.0% by weight hexanol, most preferably about 0.3–0.6% by weight hexanol. The hexanol, when used, enhances the wettability of the web during impregnation, resulting in a more uniform coating after irradiation.

The amount of the chemical solution applied to the nonwoven web may approximate the uncoated weight of the nonwoven web, or may be somewhat greater or less. If the chemical coating is too sparse, there will not be continuous coverage of the web, and the fabric product will not wick uniformly. If the chemical coating is too heavy, it may not completely react, resulting in non-uniform properties in the nonwoven web. After chemical reaction and drying, the chemical coating should add about 1–30% to the weight of the pre-coated nonwoven fabric. Suitably, the reacted chemical coating is present at about 2–20% by weight of the pre-coated nonwoven fabric, desirably about 3–12% by weight.

A process for preparing the cyclodextrin-modified layer material is schematically shown in FIG. 1. Referring to FIG. 1, a layer material, which can be a nonwoven polymer web 10, is unwound from a supply roll 12 and may, optionally, be passed through a corona treating station 14 which oxidizes at least one, and preferably both surfaces of the nonwoven web 10. The nonwoven web 10, with or without the corona treatment, is passed through a chemical coating station 16 which impregnates and preferably saturates, the web as explained below. The chemically coated nonwoven web 18 is then irradiated at an E-beam radiation station 20, which induces surface grafting of the chemical coating onto the nonwoven web, and crosslinking.

The fabric 22, which is the reaction product of the nonwoven web and chemical coating may, optionally, be rinsed or washed at the washing station 24. With or without the rinsing or washing, the fabric 22 is then dried at the drying station 26. The dried web 22 may, optionally, be further oxidized at the corona treating station 28 to effect further crosslinking of the chemical coating, and/or further reaction of the chemical coating with the nonwoven web. The fabric 22 can then be stored on rollers at station 30, and later cut for subsequent use at cutting station 32.

The optional corona treatment, which is known in the art of plastic films, involves the flow of electrical energy from a conductor to the surrounding environment. One method of treating the nonwoven web is to pass the web over a grounded metal cylinder, above which is located a high voltage electrode. The electrode is spaced from the web to leave a small gap. The corona discharge oxidizes the web surface by forming polar groups on reactive sites, making the web surface more receptive to an aqueous chemical solution. The corona treatment may be applied at a level of about 2–50 watts per square foot of web per minute, preferably about 15–40 watts per square foot per minute, more preferably about 8–12 watts per square foot per minute. Other methods of oxidizing the nonwoven web may also be employed, for example, a plasma technique.

Whether corona treated or not, the nonwoven web 10 is passed through a chemical impregnation station. The chemical impregnation may be applied by passing the nonwoven web through a solution or mixture of the chemicals, or by any suitable technique including spray coating, brushing, printing, dripping, vacuum saturation and other known methods of applying a liquid entity to a porous substrate. Preferably, the nonwoven web is passed through a solution of the chemicals, to saturate the web.

After being coated with the chemical composition, the nonwoven web is treated with radiation to graft the chemicals to the nonwoven web polymer, and to crosslink the chemical coating. Preferably, the coated nonwoven web is exposed to electron beam (E-beam) radiation as described above. Because the radiation-induced reactions are substantially complete, it is usually not necessary to rinse or wash the treated fabric 22 (FIG. 1) after irradiation and prior to use. Instead, the fabric may be passed directly into dryer 26, which is preferably a conventional through-air dryer operating at about 170–300° F. The dryer 26 removes the excess solvent (i.e., any remaining water) using air convection and evaporation. The treated fabric 22 may be rinsed or washed prior to drying, if this is desirable.

After drying, the chemically modified nonwoven fabric 22 may be stored by winding it onto a roll for later conversion, or may be directly cut and converted to use in a battery separator. Optionally, the fabric 22 may be corona treated using a second corona treatment station 28 (FIG. 1) prior to further use. The second corona treatment can be applied using the same conditions as the first corona treatment, described above, and may further oxidize and crosslink the coated fabric 22 prior to use.

The cyclodextrin-modified porous layer materials produced according to the invention are useful in a wide variety of applications. The hydrophilic nature of the cyclodextrin-modified porous layer materials renders them useful as topsheets and/or surge layers for personal care absorbent articles, including without limitation diapers, training pants, swim wear, absorbent underpants, baby wipes, adult incontinence products, and feminine hygiene articles. Additionally, the cyclodextrin-modified porous layer materials are useful for filtering small molecules which can be trapped inside the cyclodextrin cavities. The filtration aspects render the materials useful in water filters, blood filters, and controlled delivery articles for drugs, fragrances, bioactive agents, catalysts, dyes, brighteners, and the like. Other possible applications which utilize the filtration properties of the materials include protective garments for medical and industrial use.

Furthermore, the cyclodextrin-modified porous layer materials can be used as ion exchange membranes in battery separators, and in water treatment applications. The porous layer materials are useful in battery separators because they exhibit excellent wicking and durable hydrophilic properties in a highly alkaline environment, such as a solution containing 40% potassium hydroxide in water. The porous layer materials are useful in water treatment applications as filters, for instance, again because of their ability to withstand frequently alkaline environments.

EXAMPLES

The starting material for each Example uses a polypropylene meltblown nonwoven web of microfibers. The nonwoven web had a basis weight of 1.5 ounces per square yard. Each nonwoven fabric sample was initially saturated in an aqueous chemical solution having a composition described in Table 1, below.

TABLE 1

Compositions Of Chemical Solutions

| Chemical Component | Percent By Weight In Chemical Solution | | | | | |
|---|---|---|---|---|---|---|
| | Example 1 | Example 2 | Example 3 | Example 4 | Example 5 | Example 6 |
| Polyacrylic Acid | 3.5 | 0 | 1.75 | 1.75 | 3.5 | 3.5 |
| Polyethylene Glycol | 0 | 0 | 0.25 | 0.25 | 0.5 | 0.5 |
| Polyvinyl Alcohol | 0.25 | 0 | 0.125 | 0.125 | 0.25 | 0.25 |
| HMPC | 0.5 | 0.5 | 0.1 | 0.2 | 0.1 | 0.2 |
| Acrylic Acid | 1.75 | 0 | 0.875 | 0.875 | 1.75 | 1.75 |
| Hexanol | 1.0 | 1.0 | 1.0 | 1.0 | 1.0 | 1.0 |
| Water | 93 | 98.5 | 95.9 | 95.8 | 92.9 | 92.8 |

For each Example, the saturated nonwoven fabric sample was nipped between two rubber rolls to remove excess liquid and ensure uniform coverage of the nonwoven fibers. Then, each nonwoven fabric sample was irradiated at 2 or 5 mrad from an electron beam source operating at an accelerating voltage of 175 kV. After the irradiation, each nonwoven fabric sample was dried in an oven at 60° C. for 30 minutes, or until constant weight was reached.

The treated nonwoven fabric samples were then tested for vertical wicking in a 40% potassium hydroxide aqueous solution for a period of 10 minutes, using the following test procedure.

Wicking Test Procedure

This test measures the wettability of a fabric with a 40% KOH electrolyte solution.

1. Strips of fabric 0.5" wide and 3.5" long are taped to a wooden stick in the vertical direction. The strips are arranged so that there is approximately 0.25" of space between them and no more than a 0.5" under the tape.
2. The wooden stick is then clamped into an apparatus that allows the strips to hang vertically.
3. Then a pool of 40% KOH is raised up to 1 cm from the end of the strips.
4. After 10 minutes, the wicking heights are recorded and averaged.

The results of the wicking test are shown in Table 2.

TABLE 2

| | Wicking Height | | | | | | | | | | | |
|---|---|---|---|---|---|---|---|---|---|---|---|---|
| Example No. | 1 | 1 | 2 | 2 | 3 | 3 | 4 | 4 | 5 | 5 | 6 | 6 |
| Radiation Dose mrad | 2 | 5 | 2 | 5 | 2 | 5 | 2 | 5 | 2 | 5 | 2 | 5 |
| Wicking Height, cm (average of 5 measurements) | 2.8 | 3.0 | 7.1 | 7.7 | 3.8 | 3.4 | 3.9 | 4.3 | 5.6 | 6.8 | 4.5 | 6.3 |

For each Example, a radiation dose of 5 mrad resulted in better wicking than a radiation dose of 2 mrad. Example 2 in which the chemical treatment solution contained HMPC without other reactive chemicals, produced fabric samples with the highest overall wicking. Examples 5 and 6, in which the chemical treatment solution combined HMPC with significant amounts of all of the other reactive chemicals, also produced fabric samples with high overall wicking.

While the embodiments of the invention disclosed herein are presently preferred, various modifications and improvements can be made without departing from the spirit and scope of the invention. The scope of the invention is indicated by the appended claims, and all changes that fall within the meaning and range of the equivalents are intended to be embraced therein.

We claim:

1. A cyclodextrin-modified water-permeable porous layer material, comprising the chemical reaction product of:
   a hydrophobic thermoplastic porous layer material; and
   a chemical composition including a cyclodextrin compound.

2. The cyclodextrin-modified layer material of claim 1, wherein the cyclodextrin compound comprises a compound selected from the group consisting of:
   a) methacryloyl-R-cyclodextrins, wherein R is an alkyl group having 2 to 20 carbon atoms;
   b) acryloyl-R-cyclodextrins, wherein R is an alkyl group having 1 to 20 carbon atoms;
   c) alkenyl succinylated cyclodextrins, wherein the alkenyl group has 2 to 20 carbon atoms; and
   d) combinations including one or more of the foregoing compounds.

3. The cyclodextrin-modified layer material of claim 1, wherein the cyclodextrin compound comprises a methacryloyl-beta-cyclodextrin.

4. The cyclodextrin-modified layer material of claim 1, wherein the cyclodextrin compound comprises 2-hydroxy-3-methylacryloyloxy-propyl-beta cyclodextrin.

5. The cyclodextrin-modified layer material of claim 1, wherein the cyclodextrin compound has a degree of substitution of about 0.1 to about 7.

6. The cyclodextrin-modified layer material of claim 1, wherein the cyclodextrin compound comprises an alpha-cyclodextrin compound.

7. The cyclodextrin-modified layer material of claim 1, wherein the cyclodextrin compound comprises a beta-cyclodextrin compound.

8. The cyclodextrin-modified layer material of claim 1, wherein the cyclodextrin compound comprises a gamma cyclodextrin compound.

9. The cyclodextrin-modified layer material of claim 1, wherein the thermoplastic porous layer material comprises a material selected from fibrous nonwoven webs, open-celled foam layers, porous films, and combinations thereof.

10. The cyclodextrin-modified layer material of claim 1, wherein the thermoplastic porous layer material comprises a nonwoven web selected from spunbond webs, meltblown webs, carded webs, air laid webs, and combinations thereof.

11. A cyclodextrin-modified fibrous nonwoven web, comprising the radiation-induced chemical reaction product of:
    a hydrophobic thermoplastic fibrous nonwoven web; and
    a hydrophilic chemical coating including a cyclodextrin compound.

12. The cyclodextrin-modified nonwoven web of claim 11, wherein the cyclodextrin compound comprises a compound selected from the group consisting of:
    a) methacryloyl-R-cyclodextrins, wherein R is an alkyl group having 2 to 20 carbon atoms;
    b) acryloyl-R-cyclodextrins, wherein R is an alkyl group having 1 to 20 carbon atoms;
    c) alkenyl succinylated cyclodextrins, wherein the alkenyl group has 2 to 20 carbon atoms; and
    d) combinations including one or more of the foregoing compounds.

13. The cyclodextrin-modified nonwoven web of claim 11, wherein the cyclodextrin compound comprises a methacryloyl-beta-cyclodextrin.

14. The cyclodextrin-modified nonwoven web of claim 11, wherein the cyclodextrin compound comprises 2-hydroxy-3-methylacryloyloxy-propyl-beta cyclodextrin.

15. The cyclodextrin-modified nonwoven web of claim 1, wherein the cyclodextrin compound has a degree of substitution of about 0.1 to about 7.

16. The cyclodextrin-modified nonwoven web of claim 11, wherein the cyclodextrin compound comprises an alpha-cyclodextrin compound.

17. The cyclodextrin-modified nonwoven web of claim 11, wherein the cyclodextrin compound comprises a beta-cyclodextrin compound.

18. The cyclodextrin-modified nonwoven web of claim 11, wherein the cyclodextrin compound comprises a gamma cyclodextrin compound.

19. The cyclodextrin-modified nonwoven web of claim 11, wherein the hydrophilic chemical coating further comprises polyacrylic acid and acrylic acid.

20. The cyclodextrin-modified nonwoven web of claim 19, wherein the hydrophilic chemical coating further comprises polyvinyl alcohol.

21. The cyclodextrin-modified nonwoven web of claim 20, wherein the hydrophilic coating further comprises polyethylene glycol.

22. A diaper comprising the cyclodextrin-modified nonwoven web of claim 9.

23. A training pant comprising the cyclodextrin-modified nonwoven web of claim 9.

24. Swim wear comprising the cyclodextrin-modified nonwoven web of claim 9.

25. An absorbent underpant comprising the cyclodextrin-modified nonwoven web of claim 9.

26. A baby wipe comprising the cyclodextrin-modified nonwoven web of claim 9.

27. An adult incontinence product comprising the cyclodextin-modified nonwoven web of claim 9.

28. A feminine hygiene article comprising the cyclodextrin-modified nonwoven web of claim 9.

29. A water filter comprising the cyclodextrin-modified nonwoven web of claim 9.

30. A blood filter comprising the cyclodextrin-modified nonwoven web of claim 9.

31. A controlled delivery article comprising the cyclodextrin-modified nonwoven web of claim 9.

32. A protective garment comprising the cyclodextrin-modified nonwoven web of claim 9.

33. A battery separator comprising the cyclodextrin-modified nonwoven web of claim 9.

34. An ion exchange membrane for water treatment, comprising the cyclodextrin-modified nonwoven web of claim 9.

* * * * *